United States Patent [19]

Iqbal et al.

[11] 4,414,395
[45] Nov. 8, 1983

[54] PROCESS FOR THE MANUFACTURE OF HYDRAZONO-ISOINDOLINES

[75] Inventors: Abul Iqbal, Ettingen; Paul Lienhard, Frenkendorf, both of Switzerland

[73] Assignee: Ciba-Geigy Corporation, Ardsley, N.Y.

[21] Appl. No.: 241,142

[22] Filed: Mar. 6, 1981

[30] Foreign Application Priority Data

Mar. 13, 1980 [CH] Switzerland .................. 1974/80

[51] Int. Cl.³ .......................................... C07D 209/44
[52] U.S. Cl. ................................... 548/471; 564/250; 546/107
[58] Field of Search ............... 260/326.1; 564/250; 546/7; 548/471

[56] References Cited

U.S. PATENT DOCUMENTS

| 2,973,358 | 2/1961 | Pugin . | |
| 3,095,448 | 6/1963 | Biel et al. | 260/563 |
| 3,646,033 | 2/1972 | Leister et al. . | |
| 4,022,770 | 5/1977 | L'Eplattenier et al. . | |
| 4,132,708 | 1/1979 | L'Eplattenier et al. | 260/326.1 |
| 4,139,563 | 2/1979 | Metcalf et al. | 544/284 |
| 4,237,292 | 12/1980 | L'Eplattnier et al. | 546/7 |

FOREIGN PATENT DOCUMENTS

| 952810 | 10/1956 | Fed. Rep. of Germany ... 260/326.1 |
| 1219041 | 1/1971 | United Kingdom ............. 260/326.1 |
| 1467595 | 3/1977 | United Kingdom ............. 260/326.1 |

OTHER PUBLICATIONS

Thielhiemer, W.; Synthetic Methods of Organic Chemistry, vol. 21, No. 53.

Primary Examiner—Donald G. Daus
Assistant Examiner—G. Hendricks
Attorney, Agent, or Firm—Luther A. R. Hall

[57] ABSTRACT

The invention relates to a process for the manufacture of 1-hydrazono-isoindolines of the formula

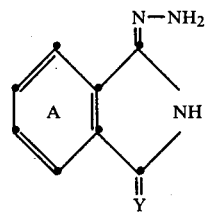

wherein Y is a methine or imine radical and the ring A can contain substituents which do not confer solubility in water, by reacting an iminoisoindoline of the formula

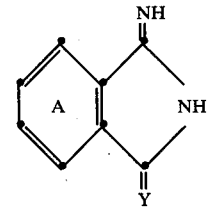

with hydrazine or a hydrazine donor, in a polar solvent, which process comprises carrying out the reaction at temperatures below 80° C.

These hydrazono-isoindolines are obtained in excellent yield and purity and can be used without further purification as starting materials for further syntheses.

5 Claims, No Drawings

PROCESS FOR THE MANUFACTURE OF HYDRAZONO-ISOINDOLINES

Hydrazono-isoindolines of the formula

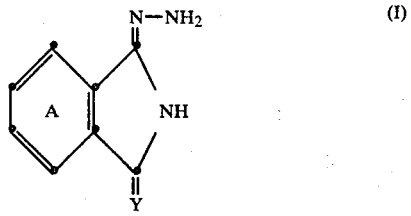

(I)

are valuable intermediates for the production of dyes and pigments. Among the methods employed for obtaining them is that which comprises reacting an iminoisoindoline of the formula

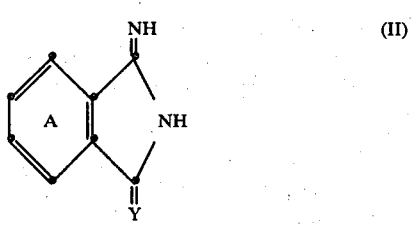

(II)

with hydrazine hydrate. The present state of the art requires for this reaction elevated temperatures in the range from about 80° to 220° C. For example, German Offenlegungsschrift 1 670 748 (Example 79) describes the reaction of 1-(cyanomethoxycarbonylmethylene)-3-iminoisoindoline with hydrazine hydrate in boiling glacial acetic acid. However, such reaction conditions lead to unsatisfactory results. Although the reaction product is obtained in good yield, it consists only part of the desired hydrazono compound, which can only be isolated in pure form from the mixture with very great difficulty. The actual yield of desired product is a mere fraction of the total amount of the mixture and does not suffice for an industrial process.

It has now been found that 1-hydrazonoisoindolines of the formula I, wherein Y is a methine or imine radical and the ring A can carry substituents that do not confer solubility in water, are obtained by reacting an iminoisoindoline of the formula II with hydrazine or a hydrazine donor, in excellent yield and purity, by carrying out the reaction at temperatures below 80° C.

The iminoisoindolines to be used as starting materials can contain halogen atoms as substituents, for example 1 to 4 chlorine atoms, 1 to 2 alkyl or alkoxy groups, each of 1 to 4 carbon atoms, a phenyl, phenoxy or nitro group, an alkanoylamino group containing 2 to 6 carbon atoms, or a benzoylamino group.

Y is preferably a methine radical of the formula

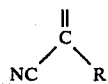

wherein R is an alkoxycarbonyl, alkylcarbamoyl, carbamoyl or sulfamoyl group, a benzylcarbamoyl group, a phenylcarbamoyl or phenylsulfamoyl group which is unsubstituted or substituted by halogen atoms or alkyl groups of 2 to 6 carbon atoms, or by nitro, cyano or trifluoromethyl groups, or is a naphthylcarbamoyl group which is unsubstituted or substituted by chlorine atoms, or a phenylsulfonyl group or a radical of the formula

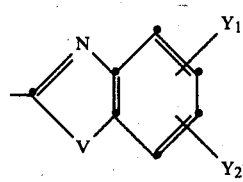

wherein V is an oxygen or a sulfur atom or an imino group, $Y_1$, $Y_2$ are hydrogen or halogen atoms, alkyl or alkoxy groups, each of 1 to 4 carbon atoms, or nitro groups.

The above specified starting materials are obtained by condensing the corresponding 1-amino-3-iminoisoindolenine with an acetonitrile of the formula NC—CH$_2$—R in the molar ratio 1:1. Representative examples are those acetonitriles listed on page 7 of British Pat. No. 1,467,595, and also cyanoaceto-o-chlorophenyl-, -p-chlorophenyl-, -m-chlorophenyl-, -m-methylphenyl-, -p-methylphenyl-, -3,4-dichlorophenyl-, -3,5-dimethylphenyl-, -3,4-dimethylphenyl, -3-chloro-4-methylphenyl-, -o-methoxyphenyl-, -2,4-dimethoxyphenyl-, -2,5-dimethoxyphenyl-, p-acetylamino-phenyl-, p-benzoylaminophenyl-, -3-chloro-4-methyl-, -p-chlorobenzoylaminophenyl-, -4-carbamoylphenyl-, -4-sulfamoylphenyl-, -4-phenylazophenyl-, -4-phenoxyphenyl-, -p-nitrophenyl-, -3-trifluoromethylphenyl-, or -2-chloro-5-trifluoromethylphenylamides, 2-cyanomethyl-4-phenyl-, -4-p-nitrophenyl-, -4-fluorophenyl- or -4-methylphenylthiazole.

An imine radical Y is derived e.g. from an aromatic amine, but preferably from a heterocyclic amine, in particular from one in which the amino group is present direct at a 5- or 6-membered heterocyclic ring which can contain 1 to 3 nitrogen atoms and, in addition, oxygen and sulfur atoms. An unsubstituted or substituted benzene nucleus can be fused to the heterocyclic parent nucleus. Representative examples are the amines listed in British Pat. No. 1,467,595, pp. 6–7, as well as 2-aminopyridine, 2-amino-5-chloropyridine, diaminophthalazine, 2-amino-4-hydroxyquinoline, 2,6-diaminopyridine, 2-amino-4,5-dimethylthiazole.

Y can also be derived from a heterocyclic compound which contains an active methylene group, for example one of those listed on pages 7 to 8 of British Pat. No. 1,467,595, as well as from 2,4-dihydroxyquinoline, 1-p-chlorophenyl-3-methyl-5-pyrazolone, 1-p-methylphenyl-3-methyl-5-pyrazolone, 1-phenyl-3-dichlorovinyl-5-pyrazolone, 1-p-methylphenyl-3-dichlorovinyl-5-pyrazolone, 1-phenyl-3-trichloroethyl-5-pyrazolone.

Preferred starting materials are iminoisoindolines of the formula

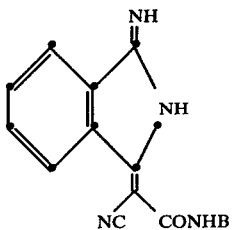

wherein B is a benzene ring which can contain halogen atoms, alkyl or alkoxy groups, each of 1 to 6 carbon atoms, alkanoylamino groups of 2 to 6 carbon atoms, a carboxamide or trifluoromethyl group or a phenoxy or benzoylamino group which is unsubstituted or substituted by halogen atoms or alkyl groups of 1 to 4 carbon atoms.

The reaction of the iminoisoindoline with the hydrazine is conducted in a polar solvent, preferably a hydrophilic solvent, for example an amide such as dimethyl formamide, formamide, dimethyl acetamide or N-methylpyrrolidone, as well as dimethyl sulfoxide, acetonitrile or an alcohol, for example ethyl cellosolve. It is also possible to use a mixture of polar solvents. To neutralise the ammonia liberated during the condensation, such a mixture can contain at least double the molar amount, based on the iminoisoindoline, of an aliphatic carboxylic acid such as glacial acetic acid. However, it is preferred to carry out the reaction in the absence of aliphatic carboxylic acids.

The reaction yields a particularly pure product if stoichiometric amounts of the hydrazine or of the hydrazine donor are employed. The reaction temperature is advantageously in the range from 10° to 40° C.

The hydrazono-isoindoline is advantageously isolated by addition of an aliphatic alcohol containing 1 to 3 carbon atoms, preferably ethanol, whereupon the final product is precipitated and can be collected by filtration. It is obtained in excellent yield and purity and can be used, without further purification, as starting material for further syntheses, especially for the condensation with aldehydes or ketones described in British Pat. No. 1,467,595 for the production of pigments. The final product can, however, also be further processed to pigments without being isolated by carrying out the reaction continuously in the same reaction vessel. Owing to the purity of the hydrazono-isoindolines obtained by the process of this invention, the pigments produced therefrom are obtained in good yield and purity.

The invention is illustrated by the following Examples.

EXAMPLE 1

11.6 g (0.06 mole) of 75% 1,3-diiminoisoindoline and 11.7 g (0.06 mole) of cyanoaceto-p-chloroanilide are dissolved in 50 ml of dimethyl formamide and 3.6 ml (0.06 mole) of glacial acetic acid and the solution is stirred overnight at room temperature (20°–23° C.). Complete reaction to 1-(cyano-p-chlorophenylcarbamoylmethylene)-3-iminoisoindoline is confirmed next day by thin-layer chromatography. Then 3.1 ml of hydrazine hydrate (0.06 mole) are added dropwise at room temperature and in the course of 1 to 2 minutes to the resultant suspension. The mixture is stirred at room temperature for 45 minutes. Subsequent analysis by thin-layer chromatography confirms that the 1-(cyano-p-chlorophenylcarbamoylmethylene)-3-iminoisoindoline is completely reacted. 250 ml of ethanol are then added to the mixture, which is thoroughly stirred at room temperature for 15–20 minutes. The precipitate is collected by filtration, washed with a small amount of ethanol and dried overnight in vacuo at 50°–60° C., affording 16.8 g (83% of theory) of the compound of the formula

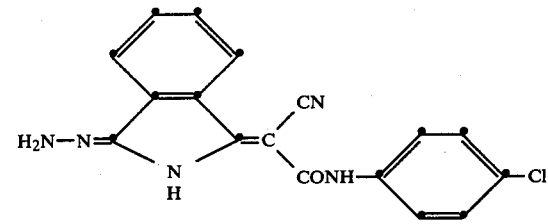

in the form of a yellowish brown powder.
Microanalysis: $C_{17}H_{12}ClN_5O$ mol. wt. 338,
 calc. 60.45% C, 3.58% H, 20.74% N, 10.50% Cl,
found 60.6% C, 3.9% H, 20.7% N, 10.5% Cl.

EXAMPLE 1B 11.6 g (0.06 mole) of 75% 1,3-diiminoisoindoline and 11.7 g (0.06 mole) of cyanoaceto-p-chloroanilide are dissolved in 50 ml of dimethyl formamide and 3.6 ml (0.06 mole) of glacial acetic acid and the solution is stirred overnight at room temperature (20°–23° C.). Complete reaction to 1-(cyano-p-chlorophenylcarbamoylmethylene)-3-iminoisoindoline is confirmed next day by thin-layer chromatography. Then 3.1 ml of hydrazine hydrate (0.06 mole) are added dropwise at room temperature and in the course of 1 to 2 minutes to the resultant suspension. The mixture is heated to 100° C. and the reaction is allowed to go to completion at the same temperature over the course of 45 minutes. The reaction mixture is then cooled to room temperature, then 250 ml of ethanol are aded, and the batch is stirred for a further 15–20 minutes at room temperature. The precipitate is collected by filtration, washed with a small amount of ethanol and dried overnight in vacuo at 50°–60° C., affording 15.8 g (78% of theory) of a brown compound which microanalysis shows to have virtually the same composition as that of the compound obtained in the same manner at room temperature in Example 1.
Microanalysis: $C_{17}H_{12}ClN_5O$ mol. wt. 338
 calc. 60.45% C, 3.58% H, 20.74% N, 10.50% Cl,
found 60.9% C, 3.4% H, 19.6% N, 10.2% Cl.

EXAMPLE 2

19.3 g (0.1 mole) of 75% 1,3-diiminoisoindoline and 16.02 g of cyanoacetanilide are dissolved in 150 ml of dimethyl formamide and 6 ml (0.1 mole) of glacial acetic acid and the solution is stirred overnight at room temperature (20°–23° C.). On the next day, 5.2 ml (0.105 mole) of hydrazine hydrate are added dropwise at room temperature and in the course of 2–3 minutes to the now yellow suspension and the mixture is stirred for 45 minutes at room temperature. Then 1000 ml of ethanol are added to the mixture, which is efficiently stirred for 15–20 minutes. The precipitate is collected by filtration, washed with a small amount of ethanol and dried overnight at 50°–60° C. in vacuo, affording 27.2 g (89.7% of theory) of the compound of the formula

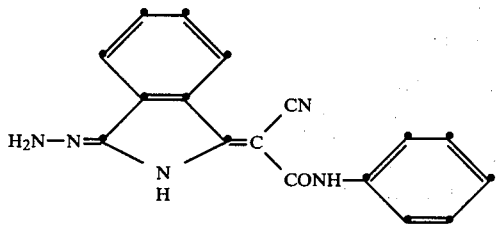

in the form of a yellow powder.
Microanalysis:
calc. (**) 66.97% C, 4.36% H, 22.97% N, found: 67.0% C, 4.3% H, 23.3% N, 0.5% H$_2$O.
(**) taking into account the 0.5% of water found.

The same product is also obtained in good yield by repeating the above procedure, but using ethyl cellosolve, formamide, dimethyl acetamide, pyrrolidone, N-methylpyrrolidone or acetonitrile instead of dimethyl formamide.

EXAMPLE 3

The procedure of Example 2 is repeated using cyanoaceto-p-toluidide instead of cyanoacetanilide. Working up yields 27 g (85% of theory) of the compound of the formula

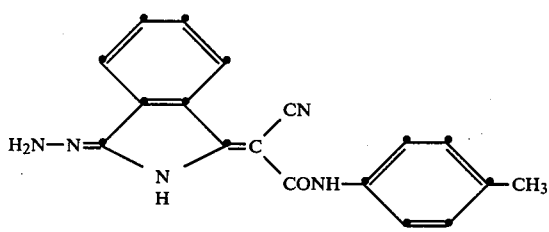

in the form of a brownish yellow powder.
Microanalysis:

calc. 68.13% C, 4.77% H, 22.07% N, found 67.9% C, 4.8% H, 22.1% N.

EXAMPLES 4 TO 6

Further hydrazones of the structure

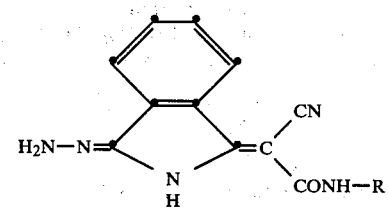

which are listed in Table 1 are obtained by procedures similar to those of Examples 1 to 3.

TABLE 1

| Example No. | R | Yield % | Microanalysis cal. % | | | found % | | |
|---|---|---|---|---|---|---|---|---|
| | | | C | H | N | C | H | N |
| 4 | -⟨⟩-O-⟨⟩ | 84 | 69.86 | 4.3 | 17.7 | 69.2 | 4.5 | 17.6 |
| 5 | OCH$_3$, -⟨⟩-O-⟨⟩-OCH$_3$, OCH$_3$ | 77 | 64.2 | 4.97 | 14.4 | 64.2 | 4.9 | 14.5 |
| 6 | -⟨⟩-N(CO-CH$_3$=CH$_3$-CO) | 67 | *62.8 | *4.4 | *19.1 | 62.5 | 4.7 | 19.0 |

*taking into account the 2.8% of water found.

EXAMPLE 7

9.8 g (0.034 mole) of 1-cyanophenylcarbamoylmethylene)-3-iminoisoindoline (prepared from 1,3-iminoisoindoline and cyanoacetanilide) are dissolved at 80°-90° C. in 95 ml of pyrrolid-2-one and the solution is then cooled to 15° C. Then 1.88 ml (0.039 mole) of hydrazine hydrate are added in the course of 1-2 minutes and the reaction mixture is stirred at room temperature 20°-23° C.) for 45 minutes. Then 200 ml of methanol are added and the mixture is stirred for 15-20 minutes at the same temperature, then cooled to 10° C. and filtered. The filter cake is washed with a small amount of methanol and dried at 60°-70° C. in vacuo, affording 6.55 g (63.5% of theory) of a compound which is chemically identical with the intermediate obtained in Example 2.

EXAMPLE 8

32.2 g (0.1 mole) of 1-(cyano-p-chlorophenylcarbamoylmethylene)-3-iminoisoindoline (prepared from 1,3-diiminoisoindoline and cyanoaceto-p-chloroanilide) are well suspended in 150 ml of dimethyl formamide.

5.2 ml (0.105 mole) of hydrazine hydrate are added dropwise at room temperature in the course of 2-3 minutes and the mixture is stirred at the same temperature for 45 minutes. Then 1000 ml of ethanol are added and the mixture is stirred thoroughly for a further 15-20 minutes at room temperature. The precipitate is isolated by filtration and washed with ethanol and dried overnight at 50°-60° C. in vacuo, affording 28.7 g (85% of theory) of a compound of the same composition as in Example 1.

EXAMPLE 9

6.24 g (0.02 mole) of 1-p-chlorophenyl-3-methyl-4-anilinomethylene-5-pyrazolone and 5.2 g (0.0204 mole) of nickel acetate tetrahydrate are dissolved in 80 ml of dimethylformamide at 60°-70° C. Then 6.7 g (0.02 mole) of the 1-(cyano-p-chlorophenylcarbamoylmethylene)-3-hydrazono-isoindoline obtained in Example 1 are stirred into the solution, and the mixture is heated to 115°-120° C. and stirred at the same temperature for a further 2 hours. Then the mixture is cooled to 80° C. and the precipitated metal complex is isolated by filtration. The filter cake is washed thoroughly with dimethyl formamide and ethanol and dried at 80° C. in vacuo, affording 9.7 g (79% of theory) of a red nickel complex of the composition $C_{28}H_{17}Cl_2N_7NiO_2$ and having the formula

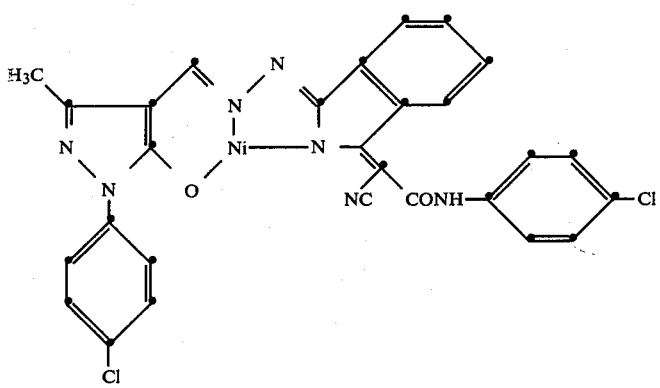

(only one of the possible isomeric or tautomeric forms is indicated).

Microanalysis: $C_{28}H_{17}Cl_2N_7NiO_2$, Mol. wt. 613.

calc. 54.85% C, 2.80% H, 15.99% N, 11.57% Cl, 9.58% Ni, found: 54.80% C, 3.1% H, 15.90% N, 11.40% Cl, 9.46% Ni.

The above 1:1 $Ni^{+2}$ complex colors PVC, plastics and lacquers in pure scarlet shades of excellent fastness to light, atmospheric influence, heat and migration.

EXAMPLE 10

The procedure of Example 9 is repeated, using the intermediate of Example 1B instead of 1-(cyano-p-chlorophenylcarbamoylmethylene)-3-hydrazono-isoindoline. Under the identical reaction conditions, a red nickel complex of the same composition as in Example 9 is obtained, but in a yield of only 3.1 g (25.3% of theory).

Microanalysis: $C_{28}H_{17}Cl_2N_7NiO_2$, Mol. wt. 613.

calc. (*) 54.49% C, 2.85% H, 15.89% N, 11.49% Cl, 9.51% Ni, found: 54.0% C, 2.9% H, 16.0% N, 11.1% Cl, 9.86% Ni, 0.7% $H_2O$.

(*) taking into account the 0.7% of water found.

This metal complex does not color PVC and lacquers in such pure shades of such good fastness to light and atmospheric influence as the metal complex pigment of Example 9.

A comparison of the yield and of the fastness properties of the metal complex pigments obtained in Examples 9 and 10 thus proves unequivocally that the process of this invention for obtaining metal complex intermediates of the 1-methylene-3-hydrazono-isoindoline type, in which the reaction is carried out preferably at room temperature (20°-40° C.), affords considerable advantages compared with the process 1B described in German Offenlegungsschrift No. 1 670 748.

EXAMPLE 11

1.1 ml (0.023 mole) of hydrazine hydrate are added dropwise at room temperature and in the course of 1-2 minutes to a mixture of 7.17 g (0.022 mole) of 1-(cyano-p-chlorophenylcarbamoylmethylene)-3-iminoisoindoline (prepared from 1,3-diiminoisoindoline and cyanaceto-p-chloroanilide) in 50 ml of dimethyl formamide. The mixture is stirred at room temperature for 40-45 minutes and subsequent analysis by thin-layer chromatography shows that the 1-(cyano-p-chlorophenylcarbamoylmethylene)-3-iminoisoindoline is completely reacted. Then a hot suspension (75°-80° C.) of 6.86 g (0.22 mole) of 1-p-chlorophenyl-3-methyl-4-anilinomethylene-5-pyrazolone and 5.75 g (0.023 mole) of nickel acetate tetrahydrate in 25 ml of dimethyl formamide is added. The mixture is heated to 115°-120° C. and stirred at the same temperature for 2 hours and then cooled to 80° C. The precipitated metal complex is isolated by filtration and the filter cake is washed thoroughly with dimethyl formamide and ethanol and dried in vacuo at 80° C., affording 10.8 g (80% of theory) of a red nickel complex having the same composition and pigment properties as in Example 9.

The metal complexes of the formula

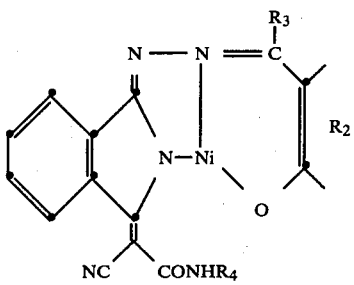

(only one of the possible tautomeric or isomeric forms is indicated) are synthesised by the continuous process of this Example. The symbols $R_2$, $R_3$ and $R_4$ are as defined in the table. Some of the starting materials are known or can be obtained by known methods.

TABLE 2

| Example | $R_2$ | $R_3$ | $R_4$ | Shade |
|---|---|---|---|---|
| 12 | [H₃C-C(=N-NH-C₆H₄-Cl)-C(CH₃)=] | H | [phenyl] | scarlet |
| 13 | " | CH₃ | " | orange |
| 14 | [o-HN-C₆H₄-attached, CH₃C(=O)-C(CH₃)=] | H | [4-Cl-C₆H₄-] | red |
| 15 | " | " | [3-Cl-4-CH₃-C₆H₃-] | orange |
| 16 | [H₂NCO-C(=N-NH-C₆H₄-CH₃)-C(CH₃)=] | H | [3-Cl-4-CH₃-C₆H₃-] | red |
| 17 | [H₂NCO-C(=N-NH-C₆H₄-CH₃)-C(CH₃)=] | H | [4-OCH₃-C₆H₄-] | scarlet |

TABLE 2-continued
| Example | R$_2$ | R$_3$ | R$_4$ | Shade |
|---|---|---|---|---|
| 18 | 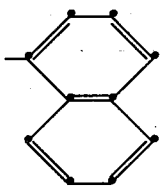 | " | naphthyl | orange |
| 19 | 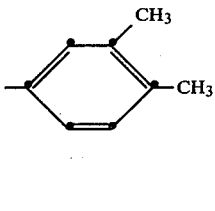 | " | 2,3-dimethylphenyl | |
| 20 | 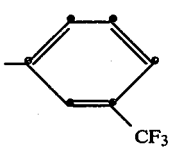 | H | 4-CF$_3$-phenyl | orange |
| 21 | 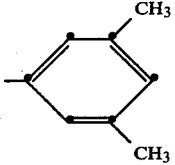 | H | 2,6-dimethylphenyl | red |
| 22 | " | " | 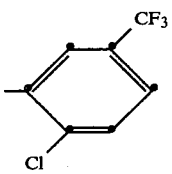 | red |

TABLE 2-continued
| Example | R₂ | R₃ | R₄ | Shade |
|---|---|---|---|---|
| 23 | 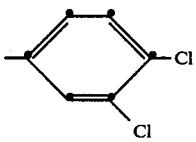 | " | 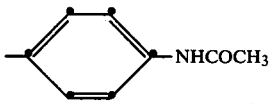 | orange |
| 24 | 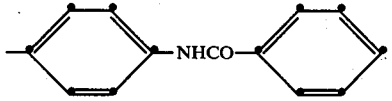 | " | 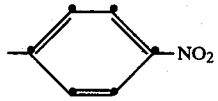 | red |
| 25 | 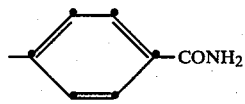 | " | (phenyl)-NHCO-(phenyl) | orange red |
| 26 | H₂NCO-pyrazole with N-N-(4-methylphenyl) | —CH₃ | (phenyl)-NO₂ | orange |
| 27 | CH₃-pyrazole with N-N-phenyl | —H— | (phenyl)-CONH₂ | red |

TABLE 2-continued

| Example | R$_2$ | R$_3$ | R$_4$ | Shade |
|---|---|---|---|---|
| 28 | 3-methyl-1-phenyl-pyrazol-5-yl (CH$_3$, N-N-phenyl) | —H— | phenyl-N=N-phenyl | orange red |
| 29 | 3-methyl-1-(4-chlorophenyl)-pyrazol-5-yl | —H— | 2-Cl-phenyl-NHCO-4-Cl-phenyl | orange |
| 30 | " | " | phenyl-SO$_2$NH$_2$ | orange |
| 31 | 3-methyl-1-(4-chlorophenyl)-pyrazol-5-yl | H | phenyl-O-phenyl | scarlet |
| 32 | " | " | phenyl-CH$_3$ | red |
| 33 | 2,6-dihydroxypyrimidin-5-yl (OH, N, HO, N) | " | 4-Cl-phenyl | yellow |

TABLE 2-continued

| Example | R₂ | R₃ | R₄ | Shade |
|---|---|---|---|---|
| 34 | (structure) | —CH₃ | (structure) | scarlet |

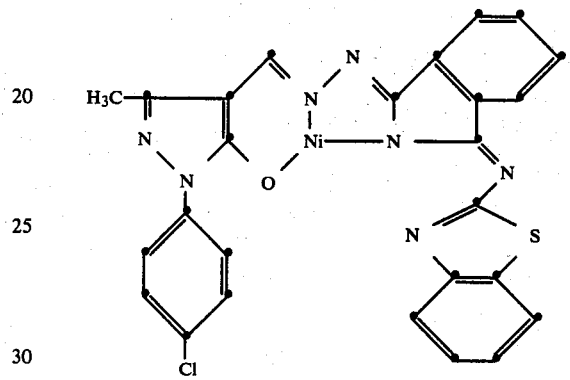

EXAMPLE 35

27.8 g (0.1 mole) of 1-(benzthiazolylimino)-3-iminoisoindoline (prepared from 1,3-diiminoisoindoline and 2-aminobenzthiazole) are suspended in 150 ml of dimethyl formamide. 5.25 ml (0.125 mole) of hydrazine hydrate are added dropwise at room temperature and in the course of 1–2 minutes and the reaction is brought to completion by stirring the mixture at the same temperature for 60 minutes. Then 650 ml of isopropanol are added and stirring is continued for 15–20 minutes at room temperature. The precipitate is collected by filtration, washed with a small amount of isopropanol and dried overnight at 50°–60° C. in vacuo, affording 13.2 g (46.3% of theory) of the compound of the formula

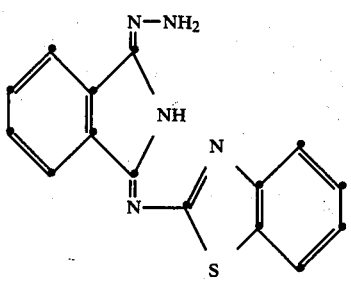

in the form of an orange yellow powder.
Microanalysis: $C_{15}H_{11}N_5S$ mol.wt. 293,3,
calc. 61.42% C, 3.78% H, 23.88% N, 10.93% S, found 60.9% C, 4.2% H, 24.2% N, 10.5% S.

Repetition of the above procedure using the above intermediate instead of the 1-(cyano-p-chlorophenyl-carbamoylmethylene)-3-hydrazono-isoindoline obtained in Example 9 gives an orange yellow nickel complex pigment of the formula (only one of the possible isomeric or tautomeric forms is indicated).

EXAMPLE 36

In accordance with the procedure of Example 8, 28.5 (0.1 mole) of 1-(cyanobenzimidazolylmethylene)-3-iminoisoindoline (prepared from 1,3-diiminoisoindoline and cyanomethylbenzimidazole) are reacted in dimethyl formamide (200 ml) at room temperature with hydrazine hydrate (5.25 ml=0.125 mole). The reaction time is 60 minutes. The reaction product is precipitated with isopropanol (650 ml) and worked up in the usual manner, affording 24 g (80% of theory) of the compound of the formula

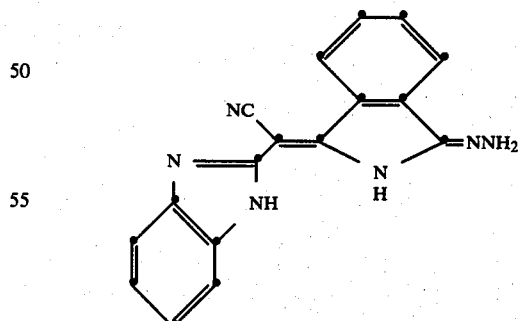

Microanalysis: $C_{17}H_{12}N_6$ mol. wt. 300.3,
found 67.99% C, 4.03% H, 27.99% N, calc. 67.9% C, 4.3% H, 27.8% N.

EXAMPLE 37

The procedure of Example 1 is repeated, using 4-chloro-1,3-diiminoisoindoline instead of 1,3- diiminoisoindoline, affording 3.87 g (57.3% of theory) of the intermediate of the formula

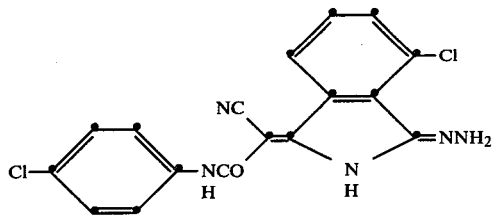

Microanalysis: $C_{17}H_{12}ClN_5O$ mol. wt. 337.8 calc. 60.45% C, 3.58% H, 20.74% N, 10.50% Cl, found 60.1% C, 3.7% H, 20.6% N, 10.6% Cl.

EXAMPLE 38

The procedure of Example 9 is repeated, using the hydrazino-isoindoline derivative of Example 36 instead of 1-(cyano-p-chlorophenylcarbamoylmethylene)-3-hydrazono-isoindoline of Example 1. Under the identical reaction conditions there is obtained a red metal complex of the formula

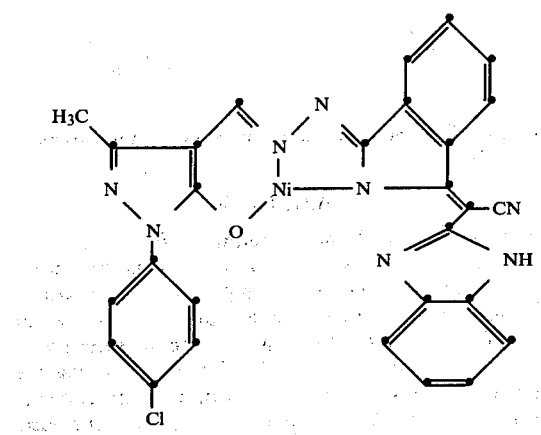

(only one of the possible isomeric or tautomeric forms is indicated)

Microanalysis: $C_{28}H_{17}ClN_8ONi$ mol.wt. 575.7, calc. 58.42% C, 2.98% H, 19.46% N, 6.16% Cl, 10.2% Ni, found 57.8% C, 3.3% H, 19.7% N, 5.6% Cl, 10.6% Ni.

With the above nickel complex it is possible to color lacquers, plastics and PVC in pure red shades having excellent fastness properties.

EXAMPLE 39

1.87 g (0.006 mole) of 1-p-chlorophenyl-3-methyl-4-anilinomethylene-5-pyrazolone and 1.57 g (0.0063 mole) of nickel acetate tetrahydrate are dissolved at 60°–70° C. in 60 ml of dimethyl formamide. Into this solution are then stirred 2.02 g (0.006 mole) of the intermediate obtained in Example 37. The mixture is heated to 110°–115° C. and stirred for a further 2 hours at this temperature. The mixture is then cooled and the precipitated metal complex is worked up as described in Example 9, affording 3.5 g (95% of theory) of a red metal complex of the formula

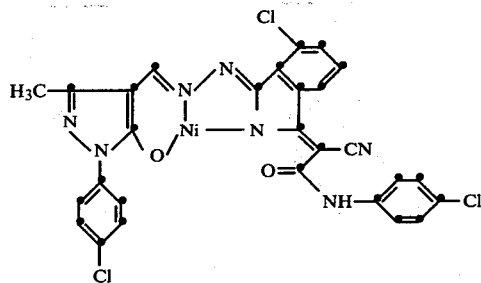

(only one of the possible isomeric or tautomeric forms is indicated).

Microanalysis: $C_{18}H_{16}Cl_3N_7O_2Ni$ mol.wt. 647.3, calc. 54.85% C, 2.80% H, 15.99% Cl, 11.57% N, 9.58% Ni, found 54.6% C, 3.0% H, 16.3% Cl, 11.4% N, 9.29% Ni.

The above metal complex colors plastics and lacquers in red shades of excellent fastness properties.

What is claimed is:

1. A process for the manufacture of a 1-hydrazono-isoindoline of the formula

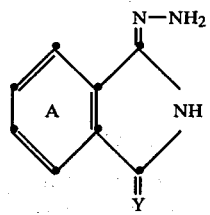

wherein

Y is a methine radical of the formula

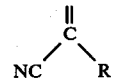

wherein R is an alkoxycarbonyl, alkylcarbamoyl, carbamoyl or sulfamoyl group, a benzylcarbamoyl group, a phenylcarbamoyl or phenylsulfamoyl group which is unsubstituted or substituted by halogen atoms or alkyl groups of 2 to 6 carbon atoms, or by nitro, cyano or trifluoromethyl groups, or is a naphthylcarbamoyl group which is unsubstituted or substituted by chlorine atoms, or a phenylsulfonyl group or a radical of the formula

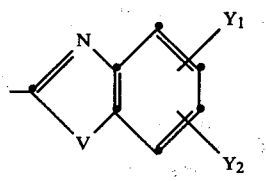

wherein V is an oxygen or a sulfur atom or an imino group, $Y_1$, $Y_2$ are hydrogen or halogen atoms, alkyl or alkoxy groups, each of 1 to 4 carbon atoms, or nitro groups, or a methine radical derived from a heterocyclic compound containing an active methylene group, or Y is an imine radical =N—E where E is the residue of an aromatic or heteroaromatic amine, the ring A is unsubstituted or is substituted by 1 to 4 chlorine atoms, 1 to 2 alkyl or alkoxy groups, each of 1 to 4 carbon atoms, a phenyl, phenoxy or nitro group, an alkanoylamino group containing 2 to 6 carbon atoms, or a benzoylamino group, consisting essentially of reacting an iminoisoindoline of the formula

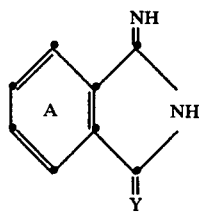

with hydrazine or hydrazine hydrate, in a polar solvent, at a temperature from 10° C. to 40° C.

2. A process according to claim 1, wherein the iminoisoindoline is of the formula

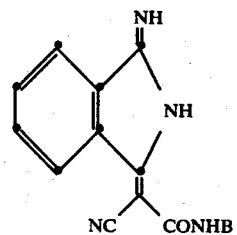

wherein B is a benzene ring which can contain halogen atoms, alkyl or alkoxy groups, each of 1 to 6 carbon atoms, alkanoylamino groups of 2 to 6 carbon atoms, a carboxamide or trifluoromethyl group, or a phenoxy or benzoylamino group unsubstituted or substituted by halogen atoms or alkyl groups of 1 to 4 carbon atoms.

3. A process according to claim 1, wherein an alcohol, an amide or imide is used as polar solvent.

4. A process according to claim 1, wherein the reaction is carried out in the absence of aliphatic carboxylic acids.

5. A process according to claim 1, wherein a stoichiometric amount of hydrazine hydrate is used.

* * * * *